(12) United States Patent
Schulat et al.

(10) Patent No.: US 7,964,147 B2
(45) Date of Patent: Jun. 21, 2011

(54) HAND-HELD ANALYSIS DEVICE

(75) Inventors: Jochen Schulat, Mannheim (DE); Jörg Scherer, Zuchwil (CH); Jürgen Rasch-Menges, Schwetzingen (DE); Josef Müller, Kirchberg SG (CH); Paul Jansen, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 656 days.

(21) Appl. No.: 11/474,861

(22) Filed: Jun. 23, 2006

(65) Prior Publication Data

US 2007/0009381 A1 Jan. 11, 2007

Related U.S. Application Data

(63) Continuation of application No. PCT/EP2004/014129, filed on Dec. 11, 2004.

(30) Foreign Application Priority Data

Dec. 24, 2003 (DE) .................................. 103 61 261

(51) Int. Cl.
*G01N 33/00* (2006.01)

(52) U.S. Cl. .................. 422/82.05; 422/400; 422/401; 422/403; 422/410

(58) Field of Classification Search .................. 422/50, 422/68.1, 82.05, 99, 400, 401, 403, 410
See application file for complete search history.

(56) References Cited

U.S. PATENT DOCUMENTS

| | | | |
|---|---|---|---|
| 5,332,549 A | 7/1994 | MacIndoe | |
| 5,575,403 A | 11/1996 | Charlton | |
| 5,645,798 A | 7/1997 | Schreiber et al. | |
| 5,971,941 A * | 10/1999 | Simons et al. | 600/573 |
| 6,475,436 B1 | 11/2002 | Schabbach et al. | |
| 2003/0039584 A1 | 2/2003 | Schabbach et al. | |
| 2003/0059350 A1 | 3/2003 | Sacherer | |

FOREIGN PATENT DOCUMENTS

| | | |
|---|---|---|
| DE | 696 09 445 T2 | 10/2004 |
| EP | 0 738 666 A2 | 10/1996 |
| EP | 0742 436 A2 | 11/1996 |
| EP | 1 284 420 A2 | 2/2003 |
| EP | 1 285 695 A2 | 2/2003 |
| EP | 1 286 162 A2 | 2/2003 |
| EP | 1 022 565 A2 | 10/2004 |
| WO | WO 97/46887 | 12/1997 |
| WO | WO 01/23885 A1 | 1/2001 |

OTHER PUBLICATIONS

"Accu-Chek Compact Blutzuckermessgerat" (Begrauchsanweisung Publ Nr. 3273571 (67)—Jun. 2001, Roche Diagnostics GmbH, Mannheim, 2001), pp. 2-3, DE.

Accu-Chek Compact Blood Glucose System (Reference Manual, Publ. Nr. 0 3307689001—Aug. 2002, Roche Diagnostics Ltd., East Sussex, 2002), pp. 2-3 IR.

* cited by examiner

*Primary Examiner* — Sam P Siefke
(74) *Attorney, Agent, or Firm* — Bose McKinney & Evans LLP

(57) ABSTRACT

The invention relates to a hand-held analytical device for analyzing a sample, in particular a biological fluid, for a medically significant component, comprising a housing comprising a loading opening for receiving a replaceable cartridge having multiple chambers that may contain analytical consumables, in particular test strips, and each chamber comprising an opening on at least one face of the cartridge and each opening may be sealed by a sealing foil, a removal facility for removing one of the analytical consumables from the cartridge. The removal facility can be used to remove one of the consumables from one of the chambers of the cartridge, in the process of which the opening sealed by the sealing foil is opened. A drive allows the cartridge to be moved in order to position one chamber in a removal position in which a consumable can be removed from the chamber by the removal facility. The invention provides for the hand-held analytical device to comprise a testing facility that can generate a signal containing information regarding whether the opening of one of the chambers is sealed by sealing foil.

36 Claims, 3 Drawing Sheets

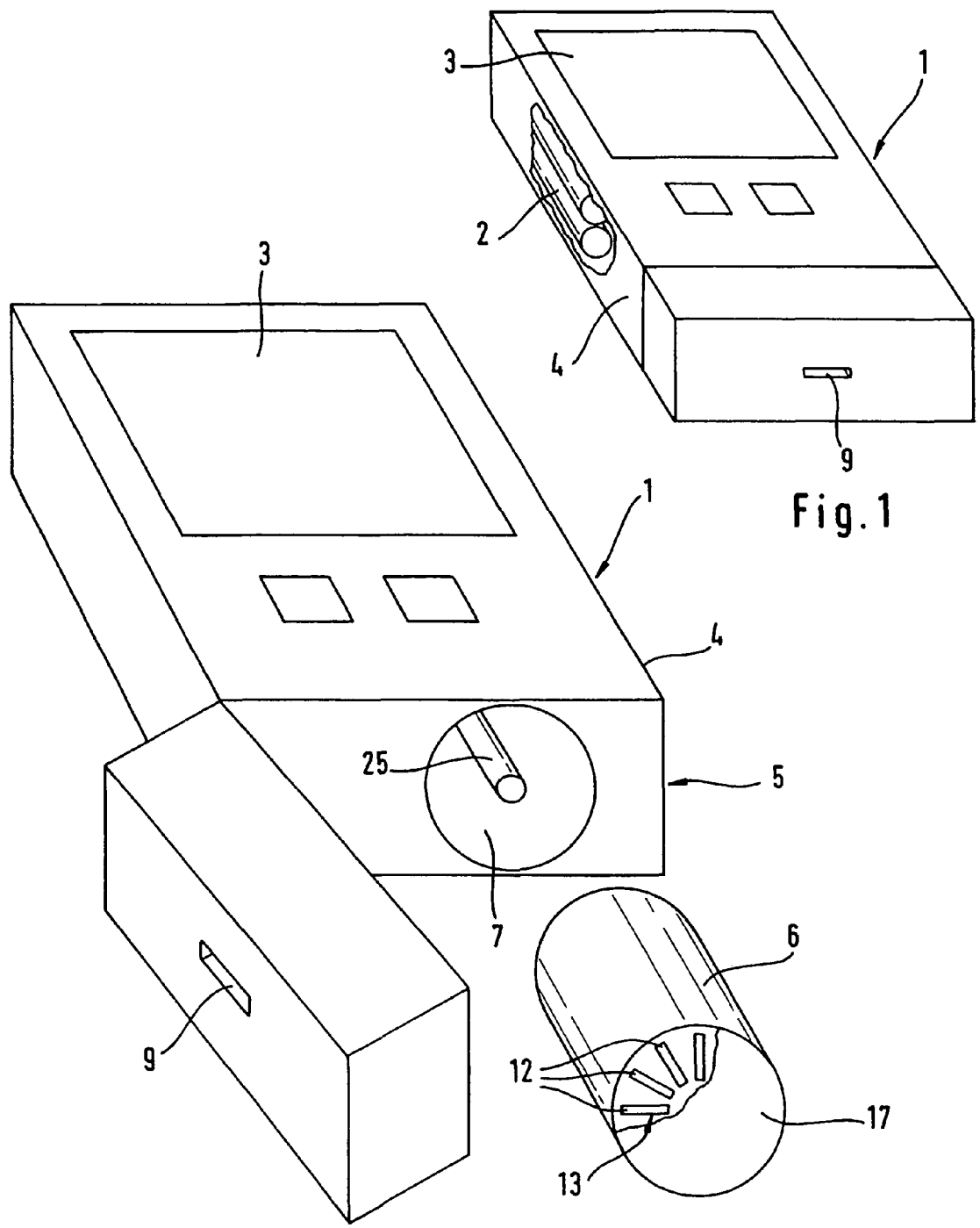
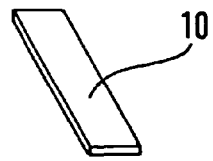

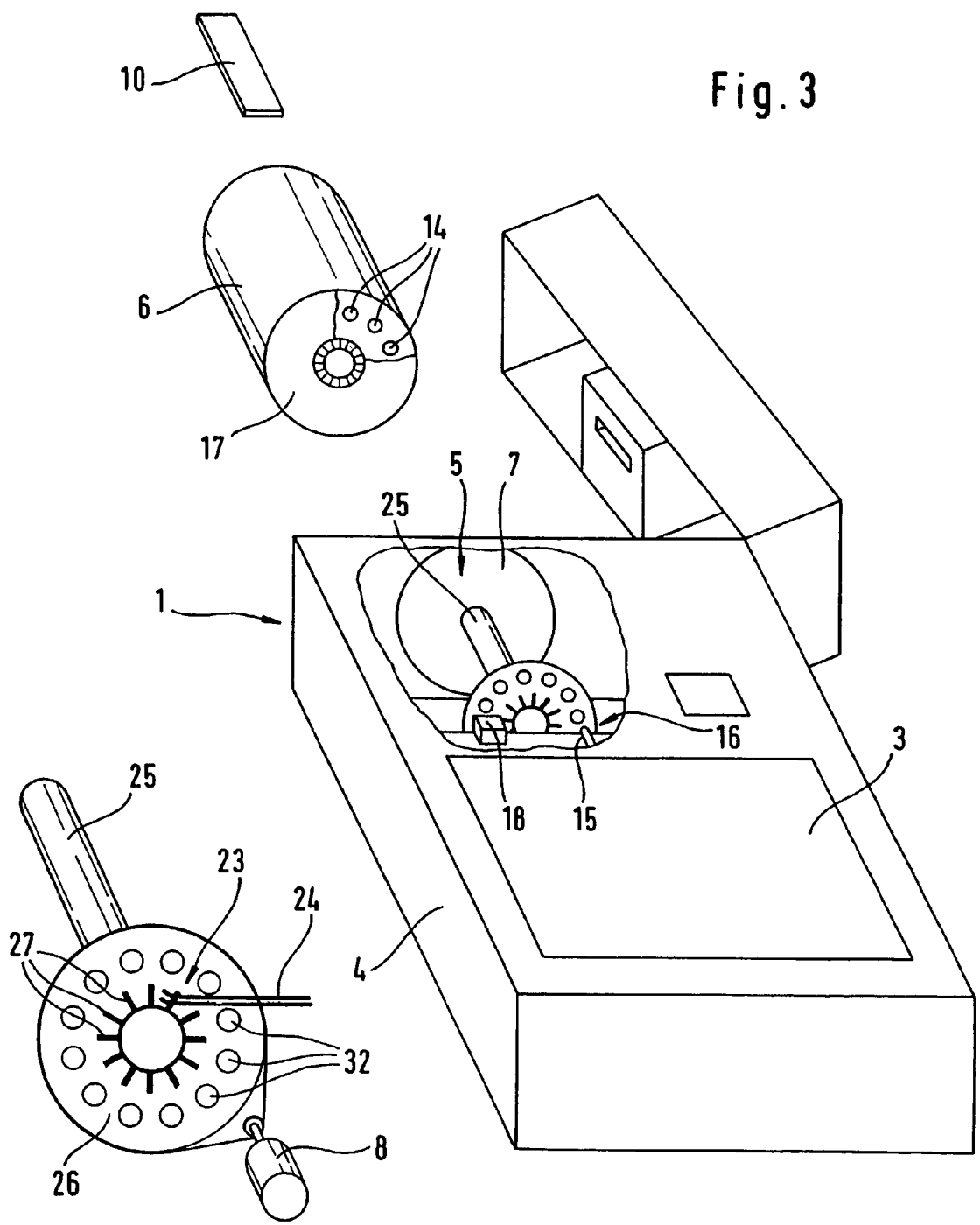

HAND-HELD ANALYSIS DEVICE

RELATED APPLICATIONS

This is a continuation application of International Application PCT/EP2004/014129, Dec. 11, 2004 which claims priority to DE 10361261.0, filed Dec. 24, 2003.

BACKGROUND

The invention relates to a hand-held analytical device for analyzing a sample, in particular a biological fluid, for a medically significant component, comprising an analytical facility, a display facility, a housing comprising a loading opening for receiving a replaceable drum cartridge having multiple chambers that may contain analytical consumables, in particular test strips, each chamber comprising an opening at a face of the cartridge, each opening may be sealed with a sealing foil, a removal facility for removing one of the analytical consumables from the cartridge. The removal facility can be used to remove one of the consumables from one of the chambers of the cartridge, in the process of which the opening sealed by the sealing foil is opened and a drive allowing the cartridge to be moved in order to position one of the chambers in a removal position in which a consumable can be removed from the chamber by means of the removal facility.

Carriers for rapid tests have become established for chemical and biochemical analysis of solid and liquid sample materials in specialized laboratories and also, in particular, for the use outside of stationary laboratories. Carriers for rapid tests are based on a specially-developed dry chemistry and can be carried out easily and straightforwardly even by laymen despite the often complex reactions involving sensitive reagents.

Test elements for the determination of the blood glucose level of diabetics are a known example of carriers for rapid tests. Diagnostic test elements provided in the form of strips are also called test strips. Known embodiments thereof include, for example, single-field or multiple-field test strips for urine analysis and various indicator papers. Since various forms of test elements other than test strips exist, test elements are more generally denoted as "analytical consumables", which also includes lancets or sample removal elements, for example.

Analytical consumables of this type are used in a hand-held analytical device which, for example, uses an optical analytical facility for analyzing by photometry a color change of a test strip. The analytical consumables are stored in a drum cartridge, such as is described, for example, in U.S. Pat. No. 6,475,436 (claiming priority to DE 19902601), which is incorporated by reference herein. A drum cartridge of this type comprises multiple chambers that can contain analytical consumables in a ring-shaped arrangement. The chambers each comprise an insertion opening and a removal opening on opposite faces of the drum cartridge. These openings each are sealed by a sealing foil in order to protect the analytical consumables from detrimental environmental influences, such as light, moisture or dust.

In known hand-held analytical devices, for example the "Accu-Chek® Compact Blutzuckermeßgerät" (Instructions for Use (German) Publ. No. 3273571 (67)-06/01, Roche Diagnostics GmbH, Mannheim, 2001), a removal facility is actuated in order to check whether or not an analytical consumable is present in or has already been removed from a chamber of the drum cartridge. The known hand-held analytical device has two testing circuits. A first testing circuit is contacted by a tappet that is attached to a pusher rod of the removal facility once that pusher rod is inserted into a chamber of the drum cartridge. If a consumable is present in the chamber, it is then pushed out by the pusher rod and actuates a switch that closes a second testing circuit. Accordingly, if an actuation of the removal facility leads to closing of the first testing circuit but not of the second testing circuit, the respective chamber of the drum cartridge is empty.

Hand-held analytical devices for analyzing a medically-relevant component of a sample, such as, for example, devices for blood glucose monitoring, are frequently handled by individuals whose perception or manual skills are impaired by disease or age. For this reason, it is important for such analytical devices to be as easy as possible to handle and maloperations to be largely excluded.

It is also important for the power consumption of hand-held analytical devices to be as low as possible. This is because, the lower the power consumption, the less frequently the batteries providing the power source of the device need to be replaced or recharged. If power consumption is sufficiently low, the use of a power source provided in the form of solar cells is possible.

All considered, contrary to stationary laboratory equipment operated by professionally trained staff, hand-held analytical devices must be as easy to handle as possible, have low power consumption, and, like the cartridges used therein, be designed to be carried by their users at all times.

SUMMARY OF THE INVENTION

The present invention provides a hand-held analytical device that can generate a signal containing information regarding whether the opening of a chamber in a cartridge containing an analytical consumable such as a test strip is sealed by a sealing foil.

In a hand-held analytical device according to one embodiment of the invention, the testing facility can be used to detect whether or not an opening of a chamber is sealed by sealing foil, i.e., whether or not the chamber contains a functional consumable. The opening is no longer sealed both after a consumable is removed and after damage occurs to the sealing foil, for example, by careless transport. The opening thus checked can be the removal opening through which a consumable is pushed and/or the insertion opening through which a pusher of the removal facility is inserted into the chamber. Since the sealing foil of both the removal opening and the insertion opening is destroyed during the removal of a consumable, the check of whether or not the consumable has already been removed can be carried out on the sealing foil of the insertion opening just as well as on the sealing foil of the removal opening. This allows avoiding unnecessary actuation of the removal facility in an attempt to remove a consumable from an empty chamber and thus significantly reduces the power consumption of the hand-held analytical device, in particular since the power consumption of a hand-held analytical device usually is largely attributable to the removal facility.

However, unsuccessful actuation of the removal facility does not only consume power, but also, and foremost, takes time. In particular, in the case of a partly empty drum cartridge that is reinserted into a hand-held analytical device after having been removed therefrom for an interim, the waiting time from the start-up of the device to the time a consumable is provided in a device according to the prior art can be disturbingly long due to, possibly, repeated unsuccessful actuation of the removal facility which then carries out successive removal attempts on already empty chambers. Advantageously, this waiting time can be significantly reduced in a hand-held analytical device according to the invention such that it is more convenient and easier to operate.

In order to reduce the power consumption of the removal facility even further, the sealing foil of a cartridge for a hand-held analytical device according to the invention can be made to be thinner and less strong than those according to the prior art such that it can be penetrated by expending less force. The strength of the sealing foil of the cartridge for a hand-held analytical device is selected as a compromise of contradictory requirements. On the one hand, the sealing foil must be penetrable by the force that can be applied by the removal facility of the hand-held analytical device. On the other hand, the sealing foil should not get damaged even during a careless transport, since this would introduce the risk of using a consumable that is adversely affected due to exposure to the environment. Since a damaged sealing foil can be detected in the case of the hand-held analytical device according to the invention, it is feasible, in order to attain the advantage provided by a removal facility consuming less power, to accept the rare risk of the sealing foil being damaged by careless transport.

Another advantage of a hand-held analytical device according to the invention is that consumables can be returned to their chamber of the cartridge after use since re-issue of a used consumable of this type can be prevented reliably. Accordingly, all consumables of a cartridge can be replaced in the cartridge after use and disposed of at the same time as the cartridge such that there is no need for a user to dispose of each consumable individually in a cumbersome fashion after completion of each test. Unlike the prior art, a hand-held analytical device according to the invention detects if a previously opened chamber containing a consumable that has been replaced therein is being provided for the removal. This chamber can then be skipped and the cartridge moved to the next chamber.

The testing facility of a hand-held analytical device according to the invention also allows for recognition of a damaged sealing foil of a chamber in which an unused consumable is present. Damage to a sealing foil is associated with an inherent risk of the consumable having been adversely affected by moisture or dirt such that a test that is carried out with this consumable might produce a false result. Consequently, the recognition of damaged sealing foil in a hand-held analytical device according to the invention can reduce the risk of using defective consumables and thus can increase the reliability of the test results.

This is a major advantage, in particular for users with reduced eyesight, in whose case the inspection of the sealing foil of each chamber of a cartridge prior to its insertion into the hand-held analytical device is associated with considerable difficulties and therefore often not done.

In the case of cartridges whose chambers comprise only a single opening serving both for delivering a consumable and for reaching-in by the removal facility, it is sufficient to have a single testing facility in order to exclude, for example, the use of consumables with an associated risk of an adverse effect due to the sealing foil being damaged. In cartridges, whose chambers comprise an insertion and a removal opening, absolute safety with regard to the inadvertent damaging of the sealing foils can be achieved only through the use of two testing facilities. In these cases though, even the use of a single testing facility at one of the openings can reduce by half the risk of using a damaged consumable or it can be recognized whether or not a consumable has already been removed from the respective chamber, regardless of the refilling thereof, if any.

The cartridge preferably is a drum cartridge that can be rotated about its geometric longitudinal axis in the hand-held analytical device. However, the invention is not limited to drum cartridges, but rather also allows for the testing of the sealing foil of a cuboid-shaped cartridge that is pushed past the delivery opening of the hand-held analytical device.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein:

FIG. 1 is a perspective view of an exemplary embodiment of a hand-held analytical device;

FIG. 2 is a perspective view with certain components exploded away that shows the exemplary embodiment of FIG. 1 with an open cartridge compartment with a drum cartridge and a consumable;

FIG. 3 is a perspective view with certain components exploded away that shows another view of the exemplary embodiment;

FIG. 4 shows an enlarged perspective view of a portion of the embodiment shown in FIG. 3.

Corresponding reference characters indicate corresponding parts throughout the several views.

DETAILED DESCRIPTION

Figure 5:
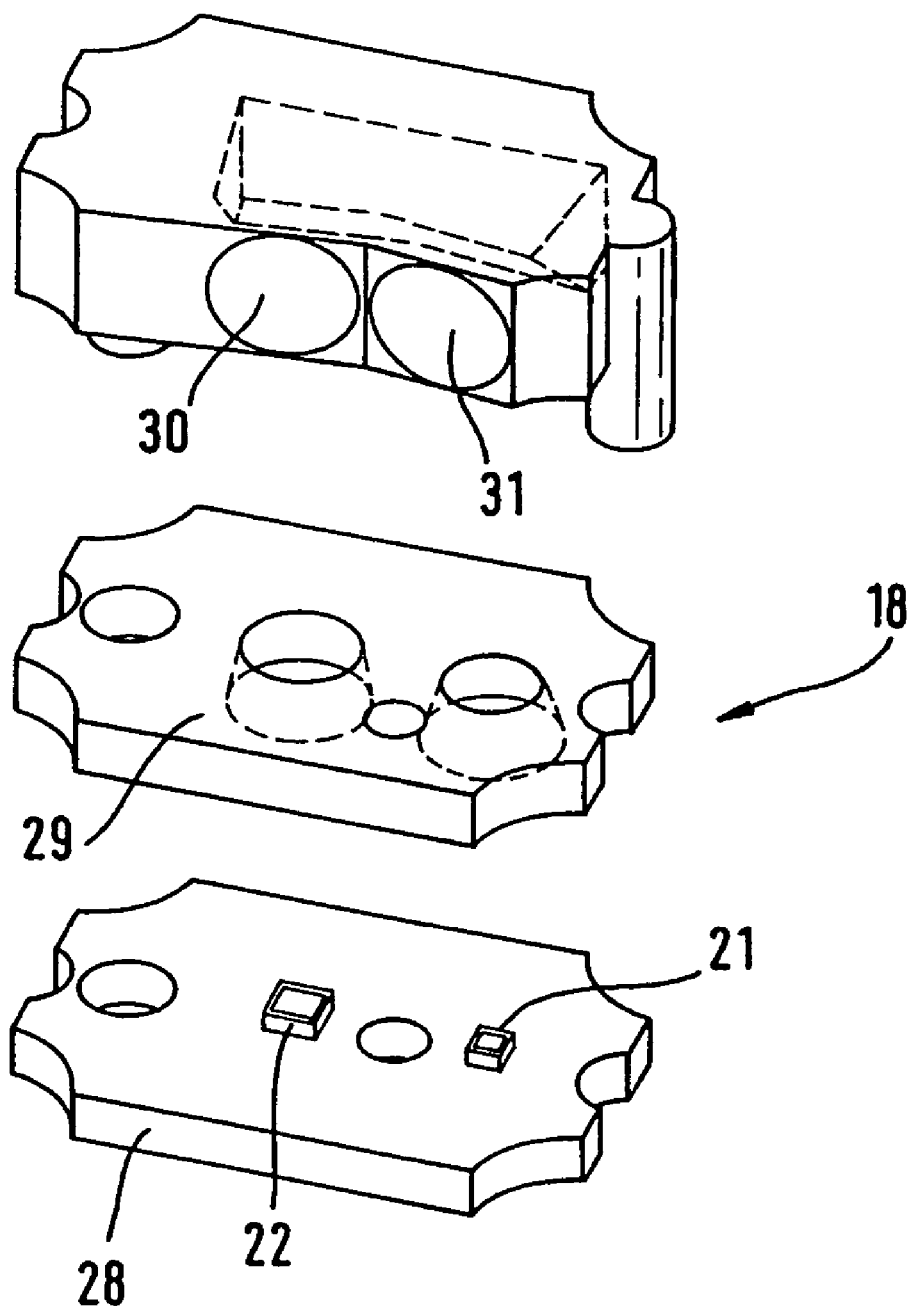
FIG. 5 is an exploded perspective view of the structure of the sensor facility in accordance with the exemplary embodiment.

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

FIGS. 1 to 3 show various views of a compact, portable hand-held analytical device 1 for testing of a medically significant component of a sample, in particular a biological fluid, such as, for example, blood, urine or saliva. The hand-held analytical device 1 shown in FIG. 1 determines blood glucose content and comprises an integrated power source in the form of commercially available batteries or solar cells. The result of a test is displayed by a display facility 3, preferably by a power-saving liquid crystal display. The hand-held analytical device 1 comprises a housing 4 with a loading opening 5 for receiving a replaceable drum cartridge 6 into a cartridge compartment or receptacle 7 in which the drum cartridge can be rotated step-wise about its geometric longitudinal axis by means of a drive. FIG. 1 shows the hand-held analytical device 1 with the loading opening 5 closed. FIGS. 2 and 3 show the hand-held analytical device 1 with the loading opening 5 open. For better illustration, a part of the housing 4 is shown in an exploded view in FIG. 4 such that a view into the cartridge compartment 7 is provided.

One face of the housing 4 comprises a delivery opening 9 for analytical consumables 10 stored in the drum cartridge 6. Preferably, these consumables 10 are provided in the form of test strips onto which a sample can be applied. A reagent contained in the test strip then reacts with a medically significant component of the sample such that the result of the reaction can be analyzed by an analytical facility of the hand-held analytical device 1. An analytical facility of this type can, for example, be an optical sensor detecting a color change of a consumable 10 that is provided in the form of a test strip, or comprise an electronic sensor determining the change in conductivity of the sample.

The drum cartridge 6 has multiple chambers 12 that are disposed in a ring-shaped arrangement about its geometric longitudinal axis and can contain analytical consumables 10. By step-wise rotation of the drum cartridge 6, the chambers 12 can be positioned consecutively or sequentially in a removal position such that the consumables 10 can be removed from the respective chamber 12 of the drum cartridge 6 and delivered through the delivery opening 9 of the housing 4 as needed.

The number of these chambers 12 can be selected virtually at will. Usually, it is useful to have 10 to 100 chambers 12, preferably, to have 15 to 30 chambers 12. Each chamber 12 comprises on one front face of the drum cartridge 6 a removal opening 13 for removing one consumable 10, and an insertion opening 14 opposite from the removal opening 13 for inserting a pusher 15 of a removal facility 16. For protection of the consumables 10, the insertion openings 14 and removal openings 13 are sealed by a sealing foil 17 that is attached or connected to the cartridge. As described in U.S. Pat. No. 6,475,436, incorporated by reference above, the pusher 15 can be used to push-out consumables 10 from chambers 12 for their use, whereby the sealing foil 17 in the area in which the insertion opening 14 is located is penetrated by the pusher 15 and the sealing foil 17 in the area in which the removal opening 13 is located is penetrated by the consumable 10.

The hand-held analytical device 1 comprises a testing facility 18 that is described in more detail with reference to FIGS. 4 and 5 and can be used to generate a signal containing information as to whether or not one of the insertion openings 14 is sealed by sealing foil 17. The testing facility 18 is connected to an analysis unit for analysis of the signal. In the exemplary embodiment shown, the testing facility 18 is arranged such that the sealing foil 17 of the chamber 12 residing in the removal position can be tested. However, it is also feasible to arrange the testing facility 18 such that it can be used to test the sealing foil 17 of a different chamber 12, which, for example, is distant from the removal position by one step of rotation.

The analysis unit comprises a memory, in which the information regarding the sealing of the respective insertion opening 14 by sealing foil 17 can be stored for each of the chambers 12. The analysis unit is connected to the display facility 3 such that an information regarding the sealing of one or multiple chambers 12 that is obtained by the analysis unit by analyzing the signal generated by the testing facility 18 can be displayed by the display facility 3. In particular, it is feasible to display to a user how many and/or which of the chambers 12 still contain a functional consumable 10.

The analysis unit comprises a control unit for controlling the drive 8 and actuates the drive 8 when an analysis of the signal concludes that the insertion opening 14 of the chamber 12 positioned for the removal of a consumable 10 is not sealed by sealing foil 17. In turn, the drive effects a rotation step of the drum cartridge 6 such that an adjacent chamber 12 is positioned in the removal position. In order to prevent unnecessary actuation of the removal facility 16 in this process, the analysis unit is connected to the removal facility 16 such that the removal facility 16 can be actuated only if the insertion opening 14 of the chamber 12 residing in the removal position that is tested by the testing facility 18 is sealed by sealing foil 17.

By this means, actuation of the removal facility 16 is always associated with the automatic removal of a consumable 10 from a chamber 12 whose insertion opening 14 is sealed by an intact sealing foil 17. Unsuccessful actuation of the removal facility 16 and ensuing insertion of the pusher 15 into an empty chamber 12 is thus avoided and the power consumption of the hand-held analytical device 1 is reduced. As a result, a user does not have to as frequently change the batteries providing the power source 2. As another advantage, there is no waiting time associated with any unsuccessful actuation of the removal facility 16 in the hand-held analytical device 1 as described. In addition, used consumables 10 can be re-inserted into their chamber 12 and stored therein after a test until all consumables 10 of a drum cartridge 6 are disposed of all at once, since the need to remove each used consumable 10 after each test is obviated.

The testing facility 18 can also be used to recognize a damaged sealing foil of an insertion opening 14. In order to be able to exclude the use of consumables 10 that are contaminated or adversely affected due to a damaged sealing foil 17 and therefore might produce unreliable test results, preferably another testing facility 18 is provided that allows the sealing foil 17 of the removal opening 13 of chambers 12 to be tested also. However, even through the use of a single testing facility 18 the risk of using a consumable 10 that is adversely affected due to a damaged sealing foil 17 can be reduced by half.

The hand-held analytical device 1 comprises a switch integrated into an opening mechanism, the actuation of which initiates a rotation of the drum cartridge 6 by 360° by closure of the cartridge compartment 7. The analysis unit uses the testing facility 18 after actuation of the switch to determine how many and/or which of the chambers 12 are (still) sealed by sealing foil 17 and displays the result by means of the display facility 3 connected to it. After insertion of a drum cartridge 6, the user can easily recognize by actuating the switch how many consumables 10 are still available in the drum cartridge 6 or which chambers 12 are still sealed by sealing foil 17.

The testing facility 18 shown in FIG. 4 and, in particular, in FIG. 5 comprises an optical detector 21 that is provided, for example, in the form of a PIN diode or a phototransistor. Moreover, the testing facility 18 comprises a light source 22 for illuminating an area of the cartridge 6 in which one of the insertion openings 14 is located. If the insertion opening 14 thus illuminated is sealed by an intact sealing foil 17, the light emitted by the light source 22 is reflected at least in part and can then be detected by the detector 21. In order to obtain a reflection signal that is as strong as possible, the sealing foil 17 has a glossy metallic surface. For this purpose, the sealing foil 17 can, for example, be provided in the form of an aluminum foil or as a metal-coated plastic film. If the sealing foil 17 is damaged, less light is reflected to the detector 21 such that an intact sealing foil 17 can be distinguished from a damaged or perforated sealing foil, meaning that an unsealed and a sealed chamber 12 can be distinguished.

For determining whether any of the chambers 12 resides in the removal position, the hand-held analytical device 1 comprises position recognition means 23 shown in FIG. 4. The position recognition means 23 preferably comprise a sliding contact 24 that can, for example, be provided in the form of a contact finger. The sliding contact 24 is arranged to be stationary with respect to the drum cartridge 6 and slides along the drum cartridge 6 or along a component of the hand-held analytical device 1 that rotates jointly with the drum cartridge 6. In the exemplary embodiment shown, the drum cartridge 6 is supported on a mandrel 25 that rotates jointly with the drum cartridge 6 and is connected to the index wheel 26.

The index wheel 26 can optionally be arranged at the front face of the drum cartridge 6 at which the insertion openings 14 reside, or on the opposite front face. The index wheel 26 shown in FIG. 4 comprises holes 32 that are located to be in alignment with the insertion openings 14 and through which the light of the testing facility 18 and the pusher 15 can penetrate. The index wheel 26 is provided with contact fields 27 that are disposed in a ring-shaped arrangement at a distance from each other and whose number corresponds to the number of chambers 12 of the drum cartridge 6. Upon a rotation of the drum cartridge 6, these contact fields 27 sequentially contact the sliding contact 24 that is provided in the form of a contact finger, such that an electric circuit is closed each time and a signal is thus generated. By counting these signals, the analysis unit can determine at which time the drum cartridge 6 has completed a full 360° rotation and which of the chambers 12 is positioned in the removal position.

In this regard, the contact fields 27 can optionally be arranged such that one of the chambers 12 is in the removal position whenever one of the contact fields 27 contacts the sliding contact 24 that is provided as a contact finger, or vice versa. Alternatively, it is also feasible to arrange the sliding contact 24 on the index wheel 26 and to arrange the contact fields 27 which act jointly with it to be fixed in place in the cartridge compartment 7.

Preferably, the signal generated by the position recognition means 23 is used to also activate the testing facility 18. This can be implemented most easily by arranging the testing facility 18 in an electric circuit that is being closed by the sliding contact 24 contacting one of the contact fields 27. The signal generated by the position recognition means 23 is preferably used to also control the drive 8 for the rotation of the drum cartridge 6, which drive 8 is provided in the form of an electric motor, such that the drive 8 automatically stops when one of the chambers 12 arrives in the removal position.

FIG. 5 illustrates in an exploded view the structure of the testing facility 18. Preferably provided in the form of an LED, the light source 22 is arranged on a plate 28 jointly with the detector 21 that is provided in the form of a phototransistor which allows for a space-saving and cost-efficient structure. In order to utilize the light of light source 22 as efficiently as possible and attain the best possible signal-to-noise ratio, the testing facility 18 comprises a lens system comprised of an aperture 29, a first lens 30, and a second lens 31. The aperture 29 resides in front of the plate 28 and serves to minimize interfering scattered light and thus increases the sensitivity of the detector 21. The first lens 30 guides light of the light source 22 to the insertion opening 14 that is to be tested such that the light emitted by the light source 22 is used as efficiently as possible. To maximize the reliability of the detection of a damaged sealing foil 17, as much of the surface as possible of the sealing foil 17 should be illuminated. Therefore, the light emitted by the light source 22 should be focused on as large of an area of the insertion opening 14 as practicable. A second lens 31 focuses the light reflected by the sealing foil 17 onto the detector 21. A one-piece injection molded part forms both the first lens 30 and the second lens 31 which eases the assembly of the testing facility 18 and renders it advantageously cost-efficient.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMBERS

1 Hand-held analytical device
2 Power source
3 Display facility
4 Housing
5 Loading opening
6 Drum cartridge
7 Cartridge compartment
8 Drive
9 Discharge (Delivery) opening
10 Consumable
12 Chamber
13 Removal opening
14 Insertion opening
15 Pusher
16 Removal facility
17 Sealing foil
18 Testing facility
21 Detector
22 Light source
23 Position recognition means
24 Sliding contact
25 Mandrel
26 Index wheel
27 Contact fields
28 Plate
29 Aperture
30 First lens
31 Second lens
32 Holes

What is claimed is:

1. A hand-held analytical device for analyzing a sample for a medically significant component, comprising:
   an analysis unit;
   a display;
   a housing comprising a loading opening for receiving a replaceable cartridge that includes multiple chambers configured to contain analytical consumables, at least one chamber comprising an opening which is initially sealed by a sealing foil;
   a drive configured to move the cartridge to position one of the chambers in a removal position;
   a removal facility configured for removing the analytical consumable from the chamber residing in the removal position, during which the sealing foil sealing the chamber residing in the removal position is opened; and
   a testing facility configured to generate a signal indicating whether the opening of one of the chambers is sealed by the sealing foil, the testing facility being connected to the analysis unit for analyzing the signal.

2. The hand-held analytical device of claim 1, wherein the testing facility is configured to test the sealing foil of the chamber residing in the removal position.

3. The hand-held analytical device of claim 1, wherein the analysis unit comprises a memory which stores information regarding whether one or more of the openings of the chambers are sealed.

4. The hand-held analytical device of claim 1, wherein the analysis unit is connected to the removal facility such that the removal facility can be actuated only if the opening of the chamber residing in the removal position that is tested by the testing facility is sealed by the sealing foil.

5. The hand-held analytical device of claim 1, wherein the analysis unit comprises a control unit for controlling the drive, whereby the analysis unit actuates the drive when the opening of the chamber residing in the removal position is not sealed by the sealing foil.

6. The hand-held analytical device of claim 1, wherein the replaceable cartridge is a drum cartridge, and, upon a rotation of the cartridge by 360°, the testing facility and the analysis unit can determine how many or which of the chambers are sealed by the sealing foil.

7. The hand-held analytical device of claim 6, further comprising a switch, the actuation of which causes the analysis unit to determine how many or which of the chambers are sealed by the sealing foil.

8. The hand-held analytical device of claim 1, wherein the analysis unit is connected to the display and the display displays information obtained by the analysis unit regarding the sealing of one or more chambers of the cartridge.

9. The hand-held analytical device of claim 8, wherein the display is configured to display how many or which of the chambers are sealed by sealing foil.

10. The hand-held analytical device of claim 1, wherein the testing facility comprises a light source and an optical detector.

11. The hand-held analytical device of claim 10, wherein the optical detector and the light source are arranged on a common plate.

12. The hand-held analytical device of claim 10, wherein the testing facility comprises an optical system for guiding light of the light source onto one of the openings or for focusing light reflected by the sealing foil onto the detector.

13. The hand-held analytical device of claim 12, wherein the optical system comprises a first lens for guiding light of the light source onto one of the openings and a second lens for focusing the light reflected by the sealing foil onto the detector.

14. The hand-held analytical device of claim 13, wherein the testing facility comprises an injection molded part in which the first and second lenses are provided.

15. The hand-held analytical device of claim 1, wherein the detector comprises a phototransistor.

16. The hand-held analytical device of claim 1, wherein the testing facility comprises a light source for illuminating one of the openings of the cartridge.

17. The hand-held analytical device of claim 16, wherein the light source comprises an LED.

18. The hand-held analytical device of claim 1, wherein the sealing foil comprises a glossy metallic surface.

19. The hand-held analytical device of claim 1, further comprising position recognition means for determining whether one of the chambers is positioned in the removal position, wherein the testing facility can be actuated by the position recognition means.

20. A hand-held analytical device for analyzing a sample for a medically significant component, comprising:
a housing having a receptacle for removably receiving a cartridge having multiple chambers containing analytical consumables, at least one chamber comprising an opening that is initially sealed by a sealing foil, the sealing foil being opened during removal of the analytical consumable;
a light source and a detector disposed in the housing, the light source configured to illuminate an area of one of the openings of a cartridge positioned in the receptacle and the detector configured to detect light reflected from the area illuminated; and
an analysis unit disposed in the housing and configured to analyze the light detected by the detector to determine whether the one opening being tested is sealed by the sealing foil.

21. The hand-held device of claim 20, wherein the analysis unit comprises a memory which stores information regarding whether one or more of the openings of the chambers are sealed.

22. The hand-held analytical device of claim 20, comprising a removal facility in communication with the analysis unit, the removal facility configured to remove the analytical consumable from a chamber of the cartridge that is positioned in a removal position, wherein the removal facility can be actuated only if the opening of the chamber residing in the removal position is determined to be sealed by the analysis unit.

23. The hand-held analytical device of claim 20, further comprising a switch, the actuation of which causes the analysis unit to determine how many or which of the chambers of a cartridge positioned in the receptacle are sealed.

24. The hand-held analytical device of claim 20, further comprising a display configured to display how many or which of the chambers are sealed by the sealing foil.

25. The hand-held analytical device of claim 20, wherein the detector and the light source are arranged on a common plate.

26. The hand-held analytical device of claim 20, further comprising a first lens for guiding light from the light source and a second lens for focusing light onto the detector.

27. The hand-held analytical device of claim 20, wherein the detector comprises a phototransistor.

28. The hand-held analytical device of claim 20, wherein the light source comprises an LED.

29. The hand-held analytical device of claim 20, further comprising an analytical facility.

30. A system for analyzing a medically significant component of a body fluid, comprising:
a cartridge, comprising:
multiple chambers containing analytical consumables, comprising at least one chamber comprising an opening; and
a sealing foil connected to the cartridge which initially seals one or more of the openings, the sealing foil being opened during removal of the analytical consumable; and
a hand-held analytical instrument, comprising:
a receptacle that removably receives the cartridge;
a light source configured to illuminate an area of the cartridge at which one of the openings is located;
a detector for detecting light reflected from the area illuminated; and
an analysis unit for analyzing the light detected by the detector and determining therefrom whether the opening being tested is sealed by the sealing foil.

31. The system of claim 30, wherein the detector comprises a phototransistor.

32. The system of claim 30, wherein the light source comprises an LED.

33. The system of claim 30, wherein the hand-held instrument comprises a display configured to display information concerning whether the opening being tested is sealed.

34. The system of claim 30, wherein the hand-held instrument further comprises a removal facility for removing the consumables from the cartridge, the removal facility being communicably connected to the analysis unit, wherein the analysis unit is configured to prevent actuation of the removal facility for any chamber of the replaceable cartridge whose opening has been determined by the analysis unit to be unsealed.

35. The system of claim 34, wherein the sealing foil comprises a glossy metallic surface.

36. The system of claim 30, wherein the hand-held instrument comprises an analytical facility wherein the analytical consumables are analyzable by the analytical facility.

* * * * *

UNITED STATES PATENT AND TRADEMARK OFFICE
CERTIFICATE OF CORRECTION

| | |
|---|---|
| PATENT NO. | : 7,964,147 B2 |
| APPLICATION NO. | : 11/474861 |
| DATED | : June 21, 2011 |
| INVENTOR(S) | : Jochen Schulat et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 864 days.

Signed and Sealed this
Fifth Day of February, 2013

Teresa Stanek Rea
*Acting Director of the United States Patent and Trademark Office*